United States Patent [19]

Ito et al.

[11] 4,056,626
[45] Nov. 1, 1977

[54] PHARMACEUTICAL COMPOSITION CONTAINING BENZOFURAN DERIVATIVE

[75] Inventors: Kiyoshi Ito, Otsu; Masahiko Ikemoto, Shiga; Kazuhiko Kimura, Otsu; Teruo Nakanishi, Kyoto, all of Japan

[73] Assignee: Kakenyaku Kako Co., Ltd., Tokyo, Japan

[21] Appl. No.: 662,099

[22] Filed: Feb. 27, 1976

Related U.S. Application Data

[60] Continuation-in-part of Ser. No. 588,195, June 19, 1975, abandoned, which is a division of Ser. No. 447,060, Feb. 28, 1974, abandoned, which is a division of Ser. No. 251,454, May 8, 1972, Pat. No. 3,853,923.

[30] Foreign Application Priority Data

| May 13, 1971 | Japan | 46-32145 |
| July 14, 1971 | Japan | 46-52333 |
| Oct. 28, 1971 | Japan | 46-86109 |
| Jan. 6, 1972 | Japan | 47-4395 |

[51] Int. Cl.² ............................................ A61K 31/34
[52] U.S. Cl. ..................................................... 424/285
[58] Field of Search ........................................... 424/285

[56] References Cited

U.S. PATENT DOCUMENTS 3,590,084   6/1971   Peperkamp et al. ............. 260/570.7

Primary Examiner—Frederick E. Waddell
Attorney, Agent, or Firm—Stevens, Davis, Miller & Mosher

[57] ABSTRACT

A pharmaceutical composition containing as the essential active ingredient a benzofuran derivative of the formula:

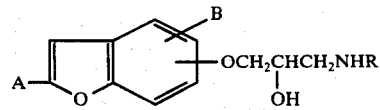

wherein A is —COR',

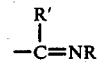

or ethyl group; B is hydrogen atom when A is —COR'

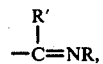

or —COR" substituted at the 3 or 4 position of the benzofuran nucleus when A is ethyl; R is an alkyl group having 1 to 5 carbon atoms; R' is an alkyl group having 1 to 4 carbon atoms, an alkoxy group having 1 to 3 carbon atoms or phenyl group; R" is an alkyl group having 1 to 4 carbon atoms, phenyl or phenylalkyl group wherein the alkyl moiety has 1 to 2 carbon atoms; and the substituted propoxy group is at the 3, 4, 5, 6 or 7 position of the benzofuran nucleus; or a pharmaceutically acceptable acid addition salt thereof in admixture with a pharmaceutically acceptable carrier. The pharmaceutical composition possesses a superior β-adrenergic blocking activity and local anesthetic activity, and is useful for the prevention and treatment of heart diseases, hypertension and hyperthyroidism.

23 Claims, No Drawings

PHARMACEUTICAL COMPOSITION CONTAINING BENZOFURAN DERIVATIVE

CROSS-REFERENCE TO RELATED APPLICATIONS

The present application is a continuation-in-part application of the copending application Ser. No. 588,195 filed on June 19, 1975 now abandoned, which is, in turn, a divisional application of the application Ser. No. 447,060 filed on Feb. 28, 1974 now abandoned, which is, in turn, a divisional application of the application Ser. No. 251,454 filed on May 8, 1972 now U.S. Pat. No. 3,853,923.

BRIEF SUMMARY OF THE INVENTION

The present invention relates to a novel pharmaceutical composition useful for the prevention and treatment of diseases in circulatory system or peripheral nervous system, for instance, heart diseases, hypertension and hyperthyroidism.

There hitherto have been known many kinds of medicaments for treating diseases in circulatory system but has still been desired further superior medicament.

It has been researched to find out other compounds useful for preventing and treating diseases in circulatory system or peripheral nervous system. As a result, it has now been found out that some novel benzofuran derivatives and their pharmaceutically acceptable acid addition salts possess superior pharmacological activities.

An object of the present invention is to provide a novel pharmaceutical composition useful for preventing and treating diseases in circulatory system or peripheral nervous system, particularly, heart diseases, hypertension and hyperthyroidism.

This and other objects will more clearly appear hereinafter.

DETAILED DESCRIPTION OF THE INVENTION

The novel benzofuran derivatives to be employed as the essential active ingredient in the pharmaceutical composition of the present invention can be illustrated by the formula (I):

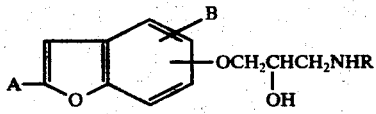

wherein A is —COR',

or ethyl group; B is hydrogen atom when A is —COR' or

or —COR" substituted at the 3 or 4 position of benzofuran nucleus when A is ethyl group; R is an alkyl group having 1 to 5 carbon atoms; R' is an alkyl group having 1 to 4 carbon atoms, an alkoxy group having 1 to 3 carbon atoms or phenyl group; R" is an alkyl group having 1 to 4 carbon atoms, phenyl group or phenylalkyl group wherein the alkyl moiety has 1 to 2 carbon atoms; and the substituted propoxy group is substituted at the 3, 4, 5, 6, or 7 position of the benzofuran nucleus.

Suitable examples of the group -COR are an alkanoyl group wherein the alkyl moiety means a straight or branched alkyl group having 1 to 4 carbon atoms, such as methyl, ethyl, propyl, isopropyl, butyl, isobutyl, secondary butyl or tertiary butyl; an alkoxycarbonyl group wherein the alkoxy moiety means an alkoxy group having 1 to 3 carbon atoms, such as methoxy, ethoxy or propoxy; and benzoyl group. Suitable examples of the group -COR" are an alkanoyl group wherein the alkyl moiety means a straight or branched alkyl group having 1 to 4 carbon atoms, such as methyl, ethyl, propyl, isopropyl, butyl or isobutyl; benzoyl group; and a phenylalkanoyl group wherein the alkyl moiety means an alkylene group having 1 to 2 carbon atoms, such as methylene or ethylene. The alkyl group defined as R is a straight or branched alkyl group having 1 to 5 carbon atoms, such as methyl, ethyl, propyl, isopropyl, butyl, isobutyl, secondary butyl, tertiary butyl or amyl, preferably a branched alkyl group having 3 to 4 carbon atoms, such as isopropyl, isobutyl, secondary butyl or tertiary butyl.

Suitable examples of the present benzofuran derivatives are 2-acetyl-7-(2-hydroxy-3-isopropylaminopropoxy)benzofuran, 2-acetyl-7-(2-hydroxy-3-tertiary butylaminopropoxy)benzofuran, 2-acetyl-4-(2-hydroxy-3-tertiary butylaminopropoxy)benzofuran, 2-carbethoxy-7-(2-hydroxy-3-isopropylaminopropoxy)benzofuran, 2-benzoyl-7-(2-hydroxy-3-isopropylaminopropoxy)benzofuran, 2-acetyl-5-(2-hydroxy-3-isopropylaminopropoxy)benzofuran, 2-acetyl-3-(2-hydroxy-3-tertiary butylaminopropoxy)benzofuran, 2-acetyl-6-(2-hydroxy-3-tertiary butylaminopropoxy)benzofuran, 2-acetyl-7-(2-hydroxy-3-secondary butylaminopropoxy)benzofuran, 2-ethyl-4-acetyl-7-(2-hydroxy-3-isopropylaminopropoxy)benzofuran, 2-ethyl-4-acetyl-7-(2-hydroxy-3-tertiary butylaminopropoxy)benzofuran, 2-ethyl-4-propionyl-7-(2-hydroxy-3-isopropylaminopropoxy)benzofuran, 2-ethyl-4-propionyl-7-(2-hydroxy-3-secondary butylaminopropoxy)benzofuran, 2-ethyl-4-benzoyl-7-(2-hydroxy-3-isopropylaminopropoxy)benzofuran, 2-ethyl-4-benzoyl-7-(2-hydroxy-3-tertiary butylaminopropoxy)benzofuran, 2-ethyl-4-phenylacetyl-7-(2-hydroxy-3-isopropylaminopropoxy)benzofuran, 2-ethyl-4-phenylacetyl-7-(2-hydroxy-3-secondary butylaminopropoxy)benzofuran, 2-ethyl-4-acetyl-5-(2-hydroxy-3-tertiary butylaminopropoxy)benzofuran, 2-ethyl-4-benzoyl-5-(2 -hydroxy-3-isopropylaminopropoxy)benzofuran, 2-ethyl-3-acetyl-7-(2-hydroxy-3-tertiary butylaminopropoxy)benzofuran, 2-ethyl-3-acetyl-5-(2-hydroxy-3-tertiary butylaminopropoxy)benzofuran, 2-(1-isopropyliminoethyl)7-(2-hydroxy-3-isopropylaminopropoxy)benzofuran, 2-(1-isopropyliminoethyl)-4-(2-hydroxy-3-isopropylaminopropoxy)benzofuran, 2-(1-secondary butyliminoethyl)-4-(2-hydroxy-3-secondary butylaminopropoxy)benzofuran, 2-(1-isopropyliminoethyl)-5-(2-hydroxy-3-isopropylaminopropoxy)benzofuran, 2-(1-secondary butyliminoethyl)-6-(2-hydroxy-3-secondary butylaminopropoxy)benzofuran and 2-(1-amyliminoethyl)5-(2-hydroxy-3-amylaminopropoxy)benzofuran. Most suitable examples are 2-acetyl-7-(2-hydroxy-3-isopropylaminopropoxy)benzofuran, 2-acetyl-7-(2-hydroxy-3-tertiary butylaminopropoxy)benzofuran, 2-acetyl-7-(2-hydroxy-3-secondary butylaminopropoxy)benzofuran, 2-carbethoxy-7-(2-hydroxy-3-isopropylaminopropoxy)benzofuran, 2-benzoyl-7-(2-hydroxy-3-isopropylaminopropoxy)benzofuran, 2-acetyl-3-(2-hydroxy-3-tertiary butylaminopropoxy)benzofuran, 2-acetyl-4-(2-hydroxy-3-tertiary butylaminopropoxy)benzofuran, 2-acetyl-5-(2-hydroxy-3-isopropylaminopropoxy)benzofuran, 2-acetyl-6-(2-hydroxy-3-tertiary butylaminopropoxy)benzofuran, 2-(1-isopropyliminoethyl)-7-(2-hydroxy-3-isopropylaminopropoxy)benzofuran, 2-(1-isopropyliminoethyl)-4-(2-hydroxy-3-isopropylaminopropoxy)benzofuran, 2-(1-secondary butyliminoethyl)-7-(2-hydroxy-3-secondary butylaminopropoxy)benzofuran, 2-(1-secondary butyliminoethyl)-4-(2-hydroxy-3-secondary butylaminopropoxy)benzofuran and 2-ethyl-4-acetyl-7-(2-hydroxy-3-isopropylaminopropoxy)benzofuran.

A method for the preparation of the present benzofuran derivatives (I) can be illustrated as follows:

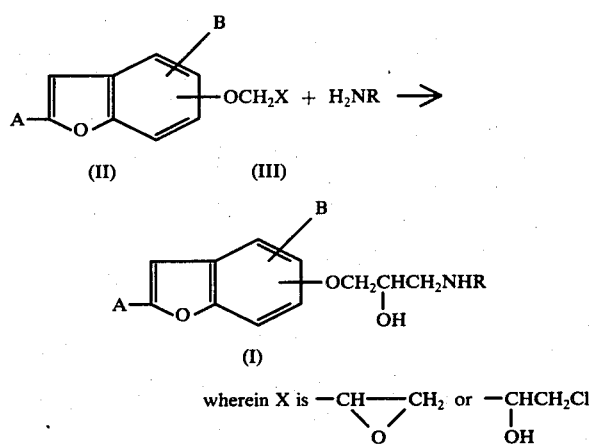

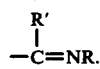

and A, B and R are the same as defined above.

In the above method, an alkoxybenzofuran derivative (II) is reacted with a primary amine (III) to give the desired benzofuran derivative (I). The reaction can be carried out at a room temperature, or at an elevated temperature, optionally under a pressure, in a suitable organic solvent such as methanol, ethanol, benzene or toluene. The reaction temperature is usually about 60° to about 110° C. and the reaction period is about 10 minutes to ten several hours, preferably about 20 minutes to about 10 hours. When A in the starting alkoxybenzofuran derivative (II) is —COR' and the reaction condition is severe, for instance, the reaction is carried out under a pressure, e.g. 2 to 50 atmospheres, preferably 3 to 10 atmospheres for a relatively long period, e.g. 10 to 15 hours, the group —COR' is also reacted with the primary amine (III) to give a group

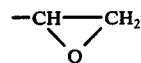

While the reaction can be carried out at an ordinary pressure when the reaction period is longer, it is preferably to carry out under a pressure. If the starting alkoxybenzofuran derivative (II) wherein X is

is used, it is preferably carried out in the presence of a mineral acid such as hydrochloric acid.

The primary amine (III) may be theoretically used in an amount of about one mole for the purpose of preparing the benzofuran derivative (I) wherein A is —COR' or ethyl group or about 2 moles for the purpose of preparing the benzofuran derivative (I) wherein A is $$\begin{array}{c} R' \\ | \\ -C=NR, \end{array}$$

per one mole of the alkoxybenzofuran derivative (II), but it is preferable to use excess amount of the primary amine (III) which functions both as reactant and solvent.

In the above method there may be used, instead of an alkoxybenzofuran derivative (II), hydroxybenzofuran derivative (IV) and epichlorohydrin (V). That is, the reaction may be also carried out by heating a mixture of hydroxybenzofuran derivative (IV), epichlorohydrin (V) and primary amine (III) at about 60° to about 110° C. for 10 minutes to ten several hours in a suitable solvent such as water, methanol, ethanol, dioxane, acetone, N,N-dimethylformamide or a mixture thereof.

The starting alkoxybenzofuran derivative (II) can be prepared by the following method:

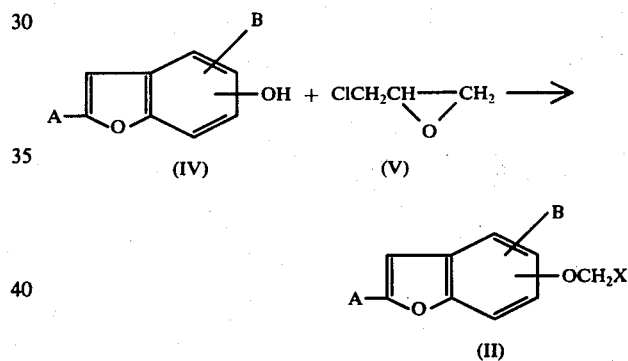

wherein A, B and X are the same as defined above.

In the method, a hydroxybenzofuran derivative (IV) is reacted with epichlorohydrin (V) to give an alkoxybenzofuran derivative (II). The reaction can be carried out by heating the reactants, optionally under a pressure, preferably in the presence of a catalyst selected from the group consisting of secondary or tertiary amines and mineral acid salts thereof; e.g. dimethylamine, diethylamine, trimethylamine, triethylamine, piperidine, pyridine, and the like. The reaction temperature is 50° to 120° C., preferably 100° to 110° C. and the reaction period is several tens minutes to ten several hours, preferably 1 to 5 hours. The reaction can be carried out without solvent, but if necessary, in a suitable organic solvent such as ethanol or N,N-dimethylformamide.

According to the above reaction, (2,3-epoxypropoxy)-benzofuran derivative (X is a group

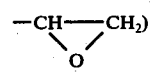

is mainly obtained and a small amount of (2-hydroxy-3-chloro)propoxybenzofuran derivative (X is a group

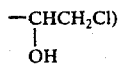

is optionally mixed with (2,3-epoxypropoxy)benzofuran derivative, but the mixture as it is can be used for the subsequent reaction. If desired, the (2,3-epoxypropoxy)-benzofuran derivative can be readily converted into (2-hydroxy-3-chloro)propoxybenzofuran derivative by treating with hydrochloric acid in a suitable organic solvent such as chloroform.

The hydroxybenzofuran derivative (IV) wherein A is ethyl and B is -COR" is a novel compound and can be readily prepared by reacting 2-ethyl-hydroxybenzofuran, in which the hydroxyl group is protected by an acyl group or a lower alkyl group, with a conventional acylating agent such as acid chloride or acid anhydride in a suitable organic solvent such as carbon disulfide, nitroethane or nitrobenzene in the presence of a catalyst such as Lewis acid, e.g. anhydrous aluminum chloride or anhydrous tin tetrachloride to introduce an acyl group at 3 or 4 position of benzofuran nucleus and removing the acyl group or alkyl group substituted on hydroxyl group by a conventional method, for example, by treating the resultant with alkali metal hydroxide, or with anhydrous aluminum chloride or anhydrous tin tetrachloride.

Alternatively, the present benzofuran derivative (I) can be also prepared by the following methods:

1. 2-alkanoyl-7-(2-hydroxy-3-aminopropoxy)benzofuran is reacted with an alkyl halide at about 60° to about 100° C. for a few hours to ten several hours in a suitable solvent such as methanol or ethanol.

2. 2-alkanoyl-7-hydroxybenzofuran or its alkali metal salt is reacted with 1-alkylamino-3-chloro-2-propanol at about 70° to about 100° C., optionally under a pressure for several hours to several tens hours.

3. 3-alkyl-5-(2-alkanoyl-7-benzofuranoxymethyl)oxazolidine or its 2-phenyl derivative is treated with an acid such as hydrochloric acid or an alkali metal hydroxide such as sodium hydroxide at about 70° to about 150° C. for several tens minutes to several hours.

4. 2-alkanoyl-7-[2-hydroxy-3-(N-acyl-N-alkyl)aminopropoxy]benzofuran is treated with an acid such as hydrochloric acid at about 70° to about 80° C. for a few hours to several hours.

5. 2-(1-ethylenedioxy)ethyl-7-(2-oxo-3-alkylaminopropoxy)benzofuran is reduced by a reducing agent such as lithium aluminum hydride, sodium borohydride or hydrogen gas-palladium catalyst or hydrogen gas-platinum catalyst at a room temperature for several tens minutes to a few hours and then the resultant is hydrolyzed with an acid such as hydrochloric acid.

6. 2-(1-ethylenedioxy)ethyl-7-[2-hydroxy-3-(N-benzyl-N-alkyl)aminopropoxy]benzofuran is reduced by hydrogen gas-palladium catalyst at a room temperature and then the resultant is hydrolyzed with an acid such as hydrochloric acid.

7. 2-(1-ethylenedioxy)ethyl-7-(2-hydroxy-3-aminopropoxy)benzofuran, 2-(1-ethylenedioxy)ethyl-7-(2-oxo-3-hydroxyiminopropoxy)benzofuran or 2-(1-ethylenedioxy)ethyl-7-(2-cyano-2-hydroxyethoxy)benzofuran is reacted with a ketone such as acetone at a lower temperature or at a room temperature under a condition of reduction, for instance, in the presence of a reducing agent such as lithium aluminum hydride or sodium borohydride or with adding hydrogen gas in the presence of a catalyst such as palladium or platinum and then the resultant is hydrolyzed with an acid such as hydrochloric acid.

8. 2-(1-ethylenedioxy)ethyl-7-(2,3-dioxopropoxy)benzofuran is reacted with a primary amine at a lower temperature under a condition of reduction as mentioned in the item (7) and then the resultant is hydrolyzed with an acid such as hydrochloric acid.

When the present benzofuran derivatives (I) prepared by the above method are a free base, they can be readily converted into their pharmaceutically acceptable acid addition salts by a conventional method, e.g. by treating the free base with an acid, if necessary, in a suitable organic solvent such as methanol or ethanol. The acid may be an inorganic acid such as hydrochloric acid, sulfuric acid or nitric acid or an organic acid such as oxalic acid, acetic acid, succinic acid, malic acid, maleic acid, tartaric acid or tannic acid. In the present invention the benzofuran derivatives (I) can be racemic, dextro- or levo-form.

The benzofuran derivatives (I) and their pharmaceutically acceptable acid addition salts possess superior pharmacological activities, particularly, superior β-adrenergic blocking activity and local anesthetic activity, and on the other hand they show low toxicity. Therefore, they are useful for the prevention and treatment of diseases in circulatory system or peripheral nervous system, particularly, heart diseases such as cardiac arrhythmias and angina pectoris, hypertension, and hyperthyroidisms such as Basedow's disease and thyrotoxicosis.

The pharmaceutical composition of the present invention contains a benzofuran derivative (I) or its pharmaceutically acceptable acid addition salt as the essential active ingredient with conventional pharmaceutically acceptable carrier. Any conventional carrier employed in preparing preparations can be employed. Examples of such carriers include binders, solid diluents, liquid diluents, fillers and the like, such as starch, lactose, microcrystalline cellose, sugar, magnesium stearate, silicon dioxide, talc and physiological salt solution.

The pharmaceutical composition of the present invention can be employed in a variety of preparation forms such as tablet, capsule, powder, granule, suspension, solution, emulsion or syrup.

The pharmaceutical composition of the present invention is administered orally or parenterally in a dosage of 10 to 800mg./day on the basis of the essential active ingredient, particularly, 10 to 200 mg./day with cardiac arrhythmias and angina pectoris, 30 to 800 mg./day with hypertension and 10 to 100 mg./day with hyperthyroidisms.

The present invention is more particularly described in the following Examples which are intended as illustrative only since numerous modifications and variations therein will be apparent to those skilled in the art.

EXAMPLE 1

To 8.8 g. of 2-acetyl-7-hydroxybenzofuran was added 80 ml. of epichlorohydrin and 0.2 g. of piperidine hydrochloride and the mixture was heated at 150° C. for 3 hours. After the reaction, the excess of epichlorohydrin was evaporated and the resultant was distilled under a reduced pressure to give 9.3 g. of 2-acetyl-7-(2,3-epoxypropoxy)benzofuran having a boiling point of 175° – 6° C./0.7 mmHg. 6 g. of the above product was dissolved in 30 ml. of ethanol and to the solution was added 10 ml. of isopropylamine. After refluxing the mixture for 40 minutes, the solvent was evaporated from the reaction mixture. The resulting residue was recrystallized from cyclohexane-acetone to give 6 g. of 2-acetyl-7-(2-hydroxy-3-isopropylaminopropoxy)benzofuran having a melting point of 115° C.

The product obtained was dissolved in 10 ml. of 3 N hydrochloric acid and thereto 50ml. of ethanol was added. The mixture was heated under a reduced pressure and the solvent was evaporated. The resulting residue was recrystallized from ethyl acetate to give its hydrochloride having a melting point of 163° C.

Analysis for $C_{16}H_{21}O_5N.HCl$: Calcd. (%) C 58.62, H 6.76, N 4.27; Found (%) C 58.32, H 6.92, N 4.07.

EXAMPLE 2

In 50 ml. of ethanol was dissolved 6 g. of 2-acetyl-7-(2,3-epoxypropoxy)benzofuran having a boiling point of 175° - 6° C./0.7 mmHg prepared in the same manner as described in Example 1 and thereto 10 ml. of tert.-butylamine was added. After refluxing the mixture for 40 minutes, the solvent was evaporated. The resulting residue was recrystallized from cyclohexane to give 6.3 g. of 2-acetyl-7-(2-hydroxy-3-tert.-butylaminopropoxy)benzofuran having a melting point of 120° C.

The product obtained was converted into its hydrochloride having a melting point of 178° C. in the same manner as described in Example 1.

Analysis for $C_{17}H_{23}O_4N.HCl$: Calcd. (%) C 59.73, H 7.08, N 4.10; Found (%) C 59.86, H 6.90, N 3.95.

EXAMPLE 3

To 3 g. of 2-acetyl-4-hydroxybenzofuran were added 30 ml. of epichlorohydrin and 150 mg. of piperidine hydrochloride and the mixture was heated at 105° C. for 2 hours. After the reaction, the excess of epichlorohydrin was evaporated. The resulting residue was recrystallized from petroleum ether-ethanol to give 3 g. of 2-acetyl-4-(2,3-epoxypropoxy)benzofuran having a melting point of 103° C. 1.2 g. of the product thus obtained was dissolved in 12 ml. of ethanol and thereto was added 5 ml. of tert.- butylamine. The mixture was refluxed for 1 hour. The solvent was evaporated from the reaction mixture to give 1.5 g. of crude 2-acetyl-4-(2-hydroxy-3-tert.- butylaminopropoxy)benzofuran. The product thus obtained was converted into 1.3 g. of its hydrochloride having a melting point of 232° C. in the same manner as in Example 1.

Analysis for $C_{17}H_{23}O_4N.HCl$: Calcd. (%) C 59.73, H 7.08, N. 4.10; Found (%) C 59.68, H 7.16, N 4.20.

EXAMPLE 4

To 1.2 g. of 2-carbethoxy-7-hydroxybenzofuran were added 30 ml. of epichlorohydrin and 120 mg. of piperidine hydrochloride. The mixture was heated at 110° C. for 2 hours. After the reaction, the excess of epichlorohydrin was evaporated and the residue was distilled to give 1.2 g. of 2-carbethoxy-7-(2,3-epoxypropoxy)benzofuran having a boiling point of 175° - 178° C./0.7 mmHg. 0.5 g. of the product thus obtained was dissolved in 5 ml. of ethanol and thereto was added 20 ml. of isopropylamine. The mixture was refluxed for one hour and then the solvent was evaporated from the reaction mixture to give 0.5 g. of crude 2-carbethoxy-7-(2-hydroxy-3-isopropylaminopropoxy)benzofuran. The crude product was recrystallized from cyclohexane-acetone to give a purified product having a melting point of 109° C.

The product thus obtained was converted into 0.4 g. of its hydrochloride having a melting point of 133° C. in the same manner as described in Example 1.

Analysis for $C_{17}H_{23}O_5N.HCl$: Calcd. (%) C 57.06, H 6.76, N 3.92; Found (%) C 57.23, H 6.85, N 3.80.

EXAMPLE 5

To 2.4 g. of 2-benzoyl-7-hydroxybenzofuran were added 30 ml. of epichlorohydrin and 150 mg. of piperidine hydrochloride. The mixture was refluxed for 3 hours. After the reaction, the excess of epichlorohydrin was evaporated. After collecting the materials dissolved into ether from the residue, the ether was evaporated to give 2.2 g. of 2-benzoyl-7-(2,3-epoxypropoxy)benzofuran as an oily substance. To the product thus obtained were added 30 ml. of ethanol and 3 g. of isopropylamine. After refluxing the mixture for 30 minutes, the solvent was evaporated. The resulting residue was recrystallized from a small amount of ether to give 2 g. of 2-benzoyl-7-(2-hydroxy-3-isopropylaminopropoxy)benzofuran having a melting point of 107° C.

Analysis for $C_{21}H_{23}O_4N$: Calcd. (%) C 71.39, H 6.56, N 3.96; Found (%) C 71.21, H 6.43, N 4.17.

EXAMPLE 6

To 2.3 g. of 2-acetyl-5-(2,3-epoxypropoxy)benzofuran which was prepared by using 2-acetyl-5-hydroxybenzofuran and epichlorohydrin in the same manner as described in Example 3 were added 20 ml. of ethanol and 5 ml. of isopropylamine. The mixture was refluxed for 40 minutes and then the excess of isopropylamine and ethanol were evaporated. To the resulting residue were added 5 ml. of diluted hydrochloric acid and further ethanol. The mixture was distilled under a reduced pressure. The residue was recrystallized from ethyl acetate-ethanol to give 2.5 g. of 2-acetyl-5-(2-hydroxy-3-isopropylaminopropoxy)benzofuran hydrochloride having a melting point of 175° C.

Analysis for $C_{16}H_{21}O_4N.HCl$: Calcd. (%) C 58.62, H 6.76, N 4.27; Found (%) C 58.41, H 6.95, N 4.03.

EXAMPLE 7

In 10 ml. of ethanol was dissolved 0.7 g. of 2-acetyl-7-(2,3-epoxypropoxy)benzofuran prepared in the same manner as described in Example 1 and thereto was added 1 g. of sec.-butylamine. After refluxing the mixture for 30 minutes, the solvent was evaporated. The resulting residue was recrystallized from cyclohexan-eacetone to give 0.8 g. of 2-acetyl-7-(2-hydroxy-3-sec.-butylaminopropoxy)benzofuran having a melting point of 82° C.

Analysis for $C_{17}H_{23}O_4N$: Calcd. (%) C 66.86, H 7.59, N 4.59; Found (%) C 66.74, N 7.62, N 4.47.

EXAMPLE 8

To 10 g. of 2-acetyl-3-hydroxybenzofuran were added 50 ml. of epichlorohydrin and 50 mg. of piperidine hydrochloride. The mixture was refluxed for 3 hours and the excess of epichlorohydrin was evaporated. The resulting residue was recrystallized from ethanol to give 6.5 g. of 2-acetyl-3-(2,3-epoxypropoxy)benzofuran having a melting point of 105.5° C. 2.2 g. of the product thus obtained was dissolved in 10 ml. of ethanol and thereto was added 4 g. of tert.-butylamine. After refluxing the mixture for 30 minutes, the solvent was evaporated under a reduced pressure. The resulting residue was recrystallized from cyclohexane to give 2 g.

of 2-acetyl-3-(2-hydroxy-3-tert.-butylaminopropoxy)-benzofuran having a melting point of 106.5° C.

Analysis for $C_{17}H_{23}O_4N$: Calcd. (%) C 66.86, H 7.59, N 4.59; Found (%) C 66.93, H 7.82, N 4.44.

EXAMPLE 9

To 1.8 g. of 2-acetyl-6-hydroxybenzofuran were added 20 ml. of epichlorohydrin and 100 mg. of piperidine hydrochloride. After refluxing the mixture for 4 hours, the excess of epichlorohydrin was evaporated. The resulting residue was recrystallized from ether-petroleum ether to give 1.2 g. of 2-acetyl-6-(2,3-epoxypropoxy)benzofuran having a melting point of 91° C. 0.5 g. of the product thus obtained was dissolved in 5 ml. of ethanol and thereto was added 1 g. of tert.-butylamine. After refluxing the mixture for 30 minutes, the solvent was evaporated. The resulting residue was recrystallized from cyclohexane-acetone to give 0.45 g. of 2-acetyl-6-(2-hydroxy-3-tert.-butylaminopropoxy)benzofuran having a melting point of 118° C.

Analysis for $C_{17}H_{23}O_4N$: Calcd. (%) C 66.86, H 7.59, N 4.59; Found (%) C 66.65, H 7.71, N 4.63.

EXAMPLE 10

In 10 ml. of epichlorohydrin was dissolved 1 g. of 2-ethyl-4-acetyl-7-hydroxybenzofuran and thereto was added 50 mg. of piperidine hydrochloride. The mixture was refluxed for 2 hours and then distilled to give 0.9 g. of 2-ethyl-4-acetyl-7-(2,3-epoxypropoxy)benzofuran. 0.4 g. of the product thus obtained and 0.2 g. of isopropylamine were added to 4 ml. of ethanol. After refluxing the mixture for 20 minutes, the solvent was evaporated under a reduced pressure. The resulting residue was recrystallized from cyclohexane containing a small amount of acetone to give 0.4 g. of 2-ethyl-4-acetyl-7-(2-hydroxy-3-isopropylaminopropoxy)benzofuran having a melting point of 115° C.

Analysis for $C_{18}H_{25}O_4N$: Calcd. (%) C 67.69, H 7.89, N 4.39; Found (%) C 67.49, H 7.86, N 4.32.

The 2-ethyl-4-acetyl-7-(2-hydroxy-3-isopropylaminopropoxy)benzofuran thus obtained was dissolved in a diluted hydrochloric acid and thereto was added ethanol. The mixture was condensed under a reduced pressure and the resulting residue was recrystallized from ethyl acetate-ethanol to give its hydrochloride having a melting point of 147° C.

Analysis for $C_{18}H_{25}O_4N.HCl$: Calcd. (%) C 60.75, H 7.36, N 3.94; Found (%) C 60.61, H 7.51, N 3.99.

The starting 2-ethyl-4-acetyl-7-hydroxybenzofuran was prepared as follows:

To 15 ml. of chlorobenzene was dissolved 1.5 g. of 2-ethyl-4-acetyl-7-methoxybenzofuran (Bull. Soc. Chim. France, 1971, page 2072) and thereto was gradually added with agitation 2 g. of finely divided anhydrous aluminum chloride at a room temperature. The mixture was heated at 70° to 80° C. for 2 hours. To the reaction mixture were added a diluted hydrochloric acid and ice. The precipitated crystallines were separated by filtration and recrystallized from benzene to give 1 g. of the desired product having a melting point of 156° to 157° C.

EXAMPLE 11

To 13 ml. of ethanol were added 1.3 g. of 2-ethyl-4-acetyl-7-(2,3-epoxypropoxy)benzofuran prepared in the same manner as described in Example 10 and 0.7 g. of tert.-butylamine. After refluxing the mixture for 20 minutes, the solvent was evaporated under a reduced pressure. The resulting residue was recrystallized from cyclohexane containing a small amount of acetone to give 1.4 g. of 2-ethyl-4-acetyl-7-(2-hydroxy-3-tert.-butylaminopropoxy)benzofuran having a melting point of 119° C.

The product thus obtained was treated hydrochloric acid in the same manner as described in Example 10 and the resulting crude crystallines were recrystallized from ethyl acetate-ethanol to give its hydrochloride having a melting point of 171° C.

Analysis for $C_{19}H_{27}O_4N.HCl$: Calcd. (%) C 61.70, H 7.63, N 3.79; Found (%) C 61.58, H 7.55, N 3.86.

EXAMPLE 12

In 15 ml. of epichlorohydrin was dissolved 0.9 g. of 2-ethyl-4-propionyl-7-hydroxybenzofuran and thereto was added 50 mg. of piperidine hydrochloride. The mixture was refluxed for 2 hours and then distilled to give 0.8 g. of 2-ethyl-4-propionyl-7-(2,3-epoxypropoxy)benzofuran. The product thus obtained and 0.65 g. of isopropylamine were added to 10 ml. of ethanol. After refluxing the mixture for 20 minutes, the solvent was evaporated under a reduced pressure. The resulting residue was recrystallized from cyclohexane to give 0.8 g. of 2-ethyl-4-propionyl-7-(2-hydroxy-3-isopropylaminopropoxy)benzofuran having a melting point of 100° C.

Analysis for $C_{19}H_6O_4N$: Calcd. (%) C 68.44, H 8.16, N 4.20; Found (%) C 68.57, H 8.12, N 4.27.

EXAMPLE 13

To 10 ml. of ethanol were added 1 g. of 2-ethyl-4-propionyl-7-(2,3-epoxypropoxy)benzofuran prepared in the same manner as described in Example 12 and 0.8 g. of sec.-butylamine. After refluxing the mixture for 20 minutes, the solvent was evaporated under a reduced pressure. The resulting residue was recrystallized from cyclohexane to give 0.9 g. of 2-ethyl-4-propionyl-7-(2-hydroxy-3-sec.-butylaminopropoxy)benzofuran having a melting point of 94° C.

Analysis for $C_{20}H_{29}O_4N$: Calcd. (%) C 69.13, H 8.41, N 4.03; Found (%) C 68.97, H 8.36, N 4.15.

EXAMPLE 14

In 13 ml. of epichlorohydrin was dissolved 0.8 g. of 2-ethyl-4-benzoyl-7-hydroxybenzofuran and thereto was added 40 mg. of piperidine hydrochloride. After refluxing the mixture for 2 hours, the reaction mixture was distilled under a reduced pressure to give 0.8 g. of 2-ethyl-4-benzoyl-7-(2,3-epoxypropoxy)benzofuran. The product thus obtained and 0.6 g. of isopropylamine were added to 10 ml. of ethanol. After refluxing the mixture for 20 minutes, the solvent was evaporated under a reduced pressure. The resulting residue was recrystallized from cyclohexane to give 0.7 g. of 2-ethyl-4-benzoyl-7-(2-hydroxy-3-isopropylaminopropoxy)benzofuran having a melting point of 94° C.

Analysis for $C_{23}H_{27}O_4N$: Calcd. (%) C 72.42, H 7.13, N 3.67; Found (%) C 72.27, H 7.11, N 3.75.

EXAMPLE 15

To 10 ml. of ethanol were added 1 g. of 2-ethyl-4-benzoyl-7-(2,3-epoxypropoxy)benzofuran prepared in the same manner as described in Example 14 and 0.7 g. of tert.-butylamine. After refluxing the mixture for 20 minutes, the solvent was evaporated under a reduced pressure. The resulting redidue was treated with hydrochloric acid in the same manner as described in Example 10. The precipitated crude crystallines were recrystallized from ethyl acetate-ethanol to give 1.2 g. of 2-ethyl-4-benzoyl-7-(2-hydroxy-3-tert.-butylaminopropoxy)benzofuran hydrochloride having a melting point of 182° C.

Analysis for $C_{24}H_{29}O_4N\cdot HCl$: Calcd. (%) C 66.74, H 7.00, N 3.24; Found (%) C 66.85, H 6.91, N 3.35.

EXAMPLE 16

In 15 ml. of epichlorohydrin was dissolved 0.84 g. of 2-ethyl-4-phenylacetyl-7-hydroxybenzofuran and thereto was added 50 mg. of piperidine hydrochloride. After refluxing the mixture for 2 hours, the reaction mixture was distilled under a reduced pressure. The resulting residue was dissolved in ether. The ether layer was taken out and ether was evaporated to give 0.7 g. of 2-ethyl-4-phenylacetyl-7-(2,3-epoxypropoxy)benzofuran. The product thus obtained and 0.5 g. of isopropylamine were added to 10 ml. of ethanol. After refluxing the mixture for 20 minutes, the solvent was evaporated under a reduced pressure. The resulting residue was recrystallized from cyclohexaneacetone to give 0.6 g. of 2-ethyl-4-phenylacetyl-7-(2-hydroxy-3-isopropylaminopropoxy)benzofuran having a melting point of 127° C.

Analysis for $C_{24}H_{29}O_4N$: Calcd. (%) C 72.88, H 7.39, N 3.54; Found (%) C 72.95, H 7.31, N 3.45.

EXAMPLE 17

To 10 ml. of ethanol were added 1 g. of 2-ethyl-4-phenylacetyl-7-(2,3-epoxypropoxy)benzofuran and 0.7 g. of sec.-butylamine. After refluxing the mixture for 20 minutes, the solvent was evaporated under a reduced pressure. The resulting residue was recrystallized from cyclohexane-acetone to give 0.95 g. of 2-ethyl-4-phenylacetyl-7-(2-hydroxy-3-sec.-butylaminopropoxy)benzofuran having a melting point of 126° C.

Analysis for $C_{25}H_{31}O_4N$: Calcd. (%) C 73.32, H 7.63, N 3.34; Found (%) C 73.51, H 7.56, N 3.33.

EXAMPLE 18

In 40 ml. of epichlorohydrin was dissolved 4 g. of 2-ethyl-4-acetyl-5-hydroxybenzofuran and thereto was added 0.1 g. of piperidine hydrochloride. After refluxing the mixture for 4 hours, the reaction mixture was distilled under a reduced pressure. The resulting residue was extracted with ether. From the ether layer, ether was evaporated and the residue was washed with petroleum ether to give 4.2 g. of 2-ethyl-4-acetyl-5-(2,3-epoxypropoxy)benzofuran. 1.5 g. of the product thus obtained and 1 g. of tert.-butylamine were added to 20 ml. of ethanol. After refluxing the mixture for 20 minutes, the solvent was evaporated under a reduced pressure. The resulting residue was extracted with a diluted hydrochloric acid. The extract was made alkaline with a diluted aqueous sodium hydroxide solution. The resulting oily substance was extracted with ether. From the ether layer, ether was evaporated to give 1.2 g. of oily substance. The oily substance was dissolved in a diluted hydrochloric acid and thereto was added ethanol. After condensing the mixture under a reduced pressure, the resulting residue was recrystallized from ethyl acetate-ether to give 1.2 g. of 2-ethyl-4-acetyl-5-(2-hydroxy-3-tert.-butylaminopropoxy)benzofuran hydrochloride having a melting point of 149° C.

Analysis for $C_{19}H_{27}O_4N\cdot HCl$: Calcd. (%) C 61.70, H 7.63, N 3.79; Found (%) C 61.53, H 7.58, N 3.65.

The starting 2-ethyl-4-acetyl-5-hydroxybenzofuran was prepared as follows:

In 30 ml. of carbon disulfide was dissolved 3.3 g. of 2-ethyl-5-n-butoxybenzofuran and thereto was added 1.35 g. of acetyl chloride. After being further added 4.7 g. of anhydrous tin tetrachloride at 0° to 5° C., the mixture was reacted at a room temperature for 3 hours, and then the solvent was evaporated. The resulting residue was dissolved in 30 ml. of chlorobenzene and thereto was added 3.2 g. of anhydrous aluminum chloride at a room temperature. The mixture was warmed at 40° to 50° C. for 2 hours. To the reaction mixture was added a cold diluted hydrochloric acid and then the mixture was extracted with ether. The ether layer was separated, dried and then ether was evaporated under a reduced pressure. To the resulting residue was added hot petroleum ether and extracted therewith. The petroleum ether layer was cooled to give 0.6 g. of the desired product having a melting point of 119.5° to 121.5° C.

EXAMPLE 19

In 12 ml. of epichlorohydrin was dissolved 1 g. of 2-ethyl-4-benzoyl-5-hydroxybenzofuran and thereto was added 70 mg. of piperidine hydrochloride. After refluxing the mixture for 3 hours, the reaction mixture was distilled under a reduced pressure. The resulting residue was extracted with ether. From the ether layer, ether was evaporated to give 1.2 g. of 2-ethyl-4-benzoyl-5-(2,3-epoxypropoxy)benzofuran as an oily substance. 1 g. of the product thus obtained and 0.7 g. of isopropylamine were added to 10 ml. of ethanol. After refluxing the mixture for 30 minutes, the solvent was evaporated under a reduced pressure. The resulting residue was recrystallized from cyclohexane to give 0.8 g. of 2-ethyl-4-benzoyl-5-(2-hydroxy-3-isopropylaminopropoxy)benzofuran having a melting point of 106° C.

Analysis for $C_{23}H_{27}O_4N$: Calcd. (%) C 77.42, H 7.13, N 3.67; Found (%) C 77.57 H 7.21, N 3.58.

EXAMPLE 20

To 2 g. of 2-ethyl-3-acetyl-7-hydroxybenzofuran were added 40 ml. of epichlorohydrin and 0.1 g. of piperidine hydrochloride. After refluxing the mixture for 2 hours, the reaction mixture was subjected to distillation under a reduced pressure to give 2.8 g. of crude 2-ethyl-3-acetyl-7-(2,3-epoxypropoxy)benzofuran. The product thus obtained and 7 ml. of tert.-butylamine were added to 20 ml. of ethanol. After refluxing the mixture for 30 minutes, the solvent was evaporated under a reduced pressure. The resulting residue was recrystallized from petroleum ether to give 1.2 g. of 2-ethyl-3-acetyl-7-(2-hydroxy-5-tert.-butylaminopropoxy)benzofuran having a melting point of 97° to 98° C.

Analysis for $C_{19}H_{27}O_4N$: Calcd. (%) C 68.44, H 8.16, N 4.20; Found (%) C 68.58, H 8.11, N 4.09.

The starting 2-ethyl-3-acetyl-7-hydroxybenzofuran was prepared as follows:

In 70 ml. of anhydrous carbon disulfide was dissolved 4.5 g. of 2-ethyl-7-acetoxybenzofuran, and thereto were further added 2 g. of acetyl chloride and 7 g. of anhydrous tin tetrachloride. The mixture was reacted at a room temperature for 2 hours. To the reaction mixture was added a cold diluted hydrochloric acid to hydrolyze. The organic layer was collected and dried, and then the solvent was evaporated to give 3 g. of crude 2-ethyl-3-acetyl-7-acetoxybenzofuran. To the product thus obtained was added a diluted aqueous sodium hydroxide solution to hydrolyze with warming and the mixture was made acidic with a diluted hydrochloric acid. The precipitated crystallines were separated by filtration and recrystallized from ethanol to give 2 g. of the desired product having a melting point of 173° to 175° C.

EXAMPLE 21

To 1.5 g. of 2-ethyl-3-acetyl-5-hydroxybenzofuran were added 30 ml. of epichlorohydrin and 0.1 g. of piperidine hydrochloride. After refluxing the mixture for 2 hours, the reaction mixture was distilled under a reduced pressure to give 2.2 g. of crude 2-ethyl-3-acetyl-5-(2,3-epoxypropoxy)benzofuran. The product thus obtained and 5 ml. of tert.-butylamine were added to 15 ml. of ethanol. After refluxing the mixture for 30 minutes, the solvent was evaporated under a reduced pressure. The resulting residue was recrystallized from petroleum ether to give 1 g. of 2-ethyl-3-acetyl-5-(2-hydroxy-3-tert.-butylaminopropoxy)benzofuran having a melting point of 114° to 115° C.

Analysis for $C_{19}H_{27}O_4N$: Calcd. (%) C 68.44, H 8.16, N 4.20; Found (%) C 68.22, H 8.05, N 4.34.

The starting 2-ethyl-3-acetyl-5-hydroxybenzofuran was prepared as follows:

In 20 ml. of anhydrous carbon disulfide was dissolved 2 g. of 2-ethyl-5-acetoxybenzofuran, and thereto were further added 0.9 g. of acetyl chloride and 3 g. of anhydrous tin tetrachloride. The mixture was reacted at a room temperature for 5 hours. To the reaction mixture was added a cold diluted hydrochloric acid to hydrolyze. The organic layer was taken out and dried, and then the solvent was evaporated to give 1.9 g. of crude 2-ethyl-3-acetyl-5-acetoxybenzofuran. To the product thus obtained was added a diluted aqueous sodium hydroxide solution to hydrolyze with warming and the mixture was made acidic with a diluted hydrochloric acid. The precipitated crystallines were separated by filtration and recrystallized from ethanol to give 1.5 g. of the desired product having a melting point of 177° to 178° C.

EXAMPLE 22

A mixture of 214 mg. of potassium salt of 2-acetyl-7-hydroxybenzofuran, 70 mg. of isopropylamine and 0.8 ml. of epichlorohydrin was suspended into 5 ml. of ethanol. After heating the suspension in a sealed tube at 100° C. for 20 hours, the reaction mixture was filtered and then the solvent was evaporated under a reduced pressure. The residue was subjected to thin layer chromatography (solid support: Kieselgel PF$_{254}$ made by E. Merck, developer: benzene-chloroform-methanol-28 % aqueous ammonia (17:4:3:0.4), eluant: chloroform) for the purification to give 2-acetyl-7-(2-hydroxy-3-isopropylaminopropoxy)benzofuran having a melting point of 115° C.

EXAMPLE 23

A mixture of 1.1 g. of 2-acetyl-7-hydroxybenzofuran, 8 ml. of epichlorohydrin and 12.5 mg. of piperidine hydrochloride was heated at 105° C. for 3 hours. The reaction mixture was condensed under a reduced pressure and dissolved in chloroform. The solution was washed with a diluted hydrochloric acid and then the solvent was evaporated to give 1.3 g. of 2-acetyl-7-(2-hydroxy-3-chloropropoxy)benzofuran. 1 g. of the product thus obtained was dissolved in 24 ml. of isopropylamine. The mixture was heated in a sealed tube at 100° C. for 12 hours. The reaction mixture was extracted with ether and the ether layer was washed with a diluted aqueous sodium hydroxide solution and then the solvent was evaporated under a reduced pressure. The resulting residue was recrystallized from cyclohexane to give 1 g. of 2-(1-isopropyliminoethyl)-7-(2-hydroxy-3-isopropylaminopropoxy)benzofuran having a melting point of 103° C.

Analysis for $C_{19}H_{28}O_3N_2$: Calcd. (%) C 68.64, H 8.49, N 8.43; Found (%) C 68.40, H 8.22, N 8.42.

EXAMPLE 24

A mixture of 1.8 g. of 2-acetyl-4-hydroxybenzofuran, 18 ml. of epichlorohydrin and 100 mg. of piperidine hydrochloride was refluxed for 4 hours. After the reaction, the solvent was evaporated under a reduced pressure. The resultant was shaken with 3 ml. of concentrated hydrochloric acid and 10 ml. of chloroform and washed with water and the chloroform layer was concentrated to give 1.4 g. of 2-acetyl-4-(2-hydroxy-3-chloropropoxy)benzofuran. The product thus obtained was dissolved in 50 ml. of isopropylamine. The solution was heated in a sealed tube at 105° C. for 14 hours and then the excess of isopropylamine was evaporated. After collecting the materials dissolved into ether from the residue, the ether was evaporated. The resulting residue was recrystallized from cyclohexane to give 1.3 g. of 2-(1-isopropyliminoethyl)-4-(2-hydroxy-3-isopropylaminopropoxy)benzofuran having a melting point of 120° C.

Analysis for $C_{19}H_{28}O_3N_2$: Calcd. (%) C 68.64, H 8.49, N 8.43; Found (%) C 68.90, H 8.26, N 8.40.

EXAMPLE 25

In 50 ml. of sec.-butylamine was dissolved 1.4 g. of 2-acetyl-4-(2-hydroxy-3-chloropropoxy)benzofuran prepared in the same manner as described in Example 24. The solution was heated in a sealed tube at 105° C. for 14 hours and then the excess of sec.-butylamine was evaporated. After collecting the materials dissolved into ether from the residue, ether was evaporated. The resulting residue was recrystallized from petroleum ether to give 1.3 g. of 2-(1-sec.-butyliminoethyl)-4-(2-hydroxy-3-sec.-butylaminopropoxy)benzofuran having a melting point of 88° C.

Analysis for $C_{21}H_{32}O_3N_2$: Calcd. (%) C 69.97, H 8.95, N 7.77; Found (%) C 69.69, H 8.87, N 7.91.

EXAMPLE 26

A mixture of 1.8 g. of 2-acetyl-5-hydroxybenzofuran, 18 ml. of epichlorohydrin and 100 mg. of piperidine hydrochloride was refluxed for 4 hours and then the solvent was evaporated. After collecting the materials dissolved into ether from the residue, ether was evaporated. The resultant was shaken with 10 ml. of chloroform and 3 ml. of concentrated hydrochloric acid and washed with water. The chloroform layer was condensed to give 1.4 g. of 2-acetyl-5-(2-hydroxy-3-chloropropoxy)benzofuran. The product thus obtained was dissolved in 50 ml. of isopropylamine. The solution was heated in a sealed tube at 105° C. for 14 hours and then the excess of isopropylamine was evaporated. After collecting the materials dissolved into ether from the residue, ether was evaporated. The resulting residue was recrystallized from petroleum ether to give 1 g. of 2-(1-isopropyliminoethyl)-5-(2-hydroxy-3-isopropylaminopropoxy)benzofuran having a melting point of 75° C.

Analysis for $C_{19}H_{28}O_3N_2$: Calcd. (%) C 68.64, H 8.49, N 8.43; Found (%) C 68.50, H 8.52, N 8.21.

EXAMPLE 27

A mixture of 1.8 g. of 2-acetyl-6-hydroxybenzofuran, 18 ml. of epichlorohydrin and 100 mg. of piperidine hydrochloride was refluxed for 4 hours and then the solvent was evaporated. The resultant was shaken with 10 ml. of chloroform and 3 ml. of concentrated hydrochloric acid and washed with water. The chloroform layer was condensed to give 1.4 g. of 2-acetyl-6-(2-hydroxy-3-chloropropoxy)benzofuran. The product thus obtained was dissolved in 50 ml. of sec.-butylamine and the solution was heated in a sealed tube at 105° C. for 14 hours and then the excess of sec.-butylamine was evaporated. After collecting the materials dissolved into ether from the residue, ether was evaporated to give 1.1 g. of 2-(1-sec.-butyliminoethyl)-6-(2-hydroxy-3-sec.-butylaminopropoxy)benzofuran as an oily substance.

Analysis for $C_{21}H_{32}O_3N_2$:
Calcd. (%) C 69.97, H 8.95, N 7.77;
Found (%) C 69.75, H 8.84, N 7.86.

EXAMPLE 28

In 26 ml. of n-amylamine was dissolved 1.3 g. of 2-acetyl-5-(2-hydroxy-3-chloropropoxy)benzofuran prepared in the same manner as described in Example 26 and the solution was heated in a sealed tube at 110° C. for 12 hours and then the excess of amylamine was evaporated under a reduced pressure. After collecting the materials dissolved into hot petroleum ether, the petroleum ether layer was cooled to give 1.3 g. of 2-(1-amyliminoethyl)-5-(2-hydroxy-3-amylaminopropoxy)benzofuran having a melting point of 70° C.

Analysis for $C_{23}H_{36}O_3N_2$:
Calcd. (%) C 71.10, H 9.34, N 7.21;
Found (%) C 70.95, H 9.30, N 7.48.

EXAMPLE 29

In 5 ml. of ethanol were dissolved 0.3 g. of 2-acetyl-7-(2-hydroxy-3-aminopropoxy)benzofuran and 1.0 g. of n-propyl bromide. The mixture was refluxed for 8 hours. After filtering the reaction mixture, the filtrate was condensed under a reduced pressure, dissolved in 5 % hydrochloric acid and washed twice with each 30 ml. of ether. The aqueous solution was made alkaline with 1.3 N aqueous sodium hydroxide solution and extracted twice with each 50 ml. of ether. The ether layer was washed with water and dried over anhydrous sodium sulfate, and then the solvent was evaporated under a reduced pressure to give 0.2 g. of yellow oily substance. The substance was allowed to stand to give 0.17 g. of 2-acetyl-7-(2-hydroxy-3-n-propylaminopropoxy)benzofuran having a melting point of 73.5° to 74.5° C.

EXAMPLE 30

To 6 ml. of methanol were added 0.6 g. of 2-acetyl-7-(2-hydroxy-3-aminopropoxy)benzofuran and 0.42 g. of isopropyl bromide. The mixture was heated in a sealed tube at 100° C. for 8 hours. After filtering the reaction mixture, the solvent was evaporated. The resulting residue was dissolved in 10 ml. of 3 N hydrochloric acid. The solution was washed twice with each 30 ml. of ether, made alkaline with 1.3 N aqueous sodium hydroxide solution and extracted three times with chloroform-ether. The solvent was evaporated from the extract under a reduced pressure to give 0.57 g. of faint yellow oily substance. The substances was allowed to stand to give 0.53 g. of 2-acetyl-7-(2-hydroxy-3-isopropylaminopropoxy)benzofuran having a melting point of 113° to 115° C.

EXAMPLE 31

To 2 ml. of ethanol were added 120 mg. of 2-acetyl-7-hydroxybenzofuran, 120 mg. of 1-isopropylamino-3-chloro-2-propanol hydrochloride and 84 mg. of powdery sodium hydroxide. The mixture was heated in a sealed tube at 70° C. for 40 hours. After filtering the reaction mixture, the solvent was evaporated under a reduced pressure. The residue was washed with 10 ml. of cyclohexane and then 10 ml. of petroleum ether in order and dissolved in 1 ml. of ethyl acetate. The solution was subjected to thin layer chromatography (solid support : Kieselgel $PF_{254}$ made by E. Merck, developer : benzene-chloroform-methanol-28 % aqueous ammonia(17 : 4 : 3 : 04), eluant : chloroform) to give 31 mg. of 2-acetyl-7-(2-hydroxy-3-isopropylaminopropoxy)benzofuran having a melting point of 113° to 115° C.

EXAMPLE 32

In 2 ml. of dimethylformamide was dissolved 0.12 g. of 2-acetyl-7-hydroxybenzofuran and thereto was added 0.42 g. of potassium carbonate. To the mixture was added 0.18 g. of 1-isopropylamino-2-hydroxy-3-chloropropane hydrochloride in portions (5 times) over 1 hour with agitation at 80° to 100° C., and the mixture was heated with agitiation at 80° to 100° C. for 8 hours. The reaction mixture was filtered and distilled under a reduced pressure. The residue was extracted with chloroform. The chloroform layer was separated and chloroform was evaporated. The residue was dissolved in 50 ml. of ether and then extracted with 3 N hydrochloric acid. The extract was made alkaline with 1.3 N aqueous sodium hydroxide solution and extracted with chloroform. The chloroform layer was washed with water, dried over anhydrous sodium sulfate and then the solvent was condensed. The resultant was subjected to thin layer chromatography (solid support: Kieselgel $PF_{254}$ made by E. Merck, developer: benzene-chloroform-methanol-28 % aqueous ammonia (17 : 4 : 3 : 0.4), eluant: chloroform) to give 29 mg. of 2-acetyl-7-(2-hydroxy-3-isopropylaminopropoxy)benzofuran having a melting point of 113° to 115° C.

EXAMPLE 33

In a mixture of 1 ml. of acetone and 2 ml. of methanol was dissolved 0.2 g. of 2-(1-ethylenedioxy)ethyl-7-(2-hydroxy-3-aminopropoxy)benzofuran. To the mixture was added in portions 0.2 g. of sodium borohydride with agitation under cooling and further 3 drops of acetic acid and 5 drops of concentrated hydrochloric acid in order. After filtering the mixture, the filtrate was distilled under a reduced pressure to give faint yellow crystallines. The product thus obtained was dissolved in ethyl acetate-methanol (2 : 1). The solution was filtered, distilled under a reduced pressure, made alkaline with 3 N aqueous sodium hydroxide solution and then extracted with ether. The ether layer was dried over anhydrous sodium sulfate and ether was evaporated to give 0.15 g. of 2-acetyl-7-(2-hydroxy-3-isopropylaminopropoxy)benzofuran having a melting point of 115° C.

EXAMPLE 34

In 30 ml. of methanol was dissolved 1.0 g. of 2-(1-ethylenedioxy)ethyl-7-(2-hydroxy-3-aminopropoxy)-benzofuran and thereto were added 10 ml. of acetone and 0.8 g. of 5 % palladium-charcoal. To the mixture was added hydrogen gas at a room temperature under atmospheric pressure until theoretical amount of hydrogen was absorbed. The reaction mixture was filtered and distilled under a reduced pressure to give 1.0 g. of faint yellow oily substance. The substance was dissolved in 20 ml. of ethanol and thereto was added 0.1 ml. of concentrated hydrochloric acid. The mixture was agitated at a room temperature for 30 minutes and then the solvent was evaporated under a reduced pressure. To the residue was added 5 ml. of 3 N hydrochloric acid and the mixture was extracted with ether, made alkaline with 1.3 N aqueous sodium hydroxide solution and extracted twice with etherchloroform (1 : 1). The solvent was evaporated to give 0.97 g. of 2-acetyl-7-(2-hydroxy-3-isopropylaminopropoxy)benzofuran having a melting point of 113° to 115° C.

EXAMPLE 35

A mixture of 1.0 g. of 3-isopropyl-5-(2-acetyl-7-benzofuranoxymethyl)oxazolidone and 10 ml. of 10 N aqueous sodium hydroxide solution was heated with agitation at 150° C. for 30 minutes. To the reaction mixture was added 100 ml. of water and the mixture was made slightly alkaline with a diluted hydrochloric acid and extracted with chloroformether. The organic layer was dried over anhydrous sodium sulfate and the solvent was evaporated under a reduced pressure to give 0.6 g. of 2-acetyl-7-(2-hydroxy-3-isopropylaminopropoxy)benzofuran having a melting point of 113° to 115° C.

EXAMPLE 36

To 10 ml. of 10 % hydrochloric acid was added 1.0 g. of 2-phenyl-3-isopropyl-5-(2-acetyl-7-benzofuranoxymethyl)oxazolidine and the mixture was heated at 90° to 95° C. for one hour. After cooling, the reaction mixture was made alkaline with 1.3 N aqueous sodium hydroxide solution and extracted with etherchloroform. The organic layer was washed with water, dried over anhydrous sodium sulfate and the solvent was evaporated under a reduced pressure to give 0.9 g. of 2-acetyl-7-(2-hydroxy-3-isopropylaminopropoxy)benzofuran having a melting point of 113° to 115° C.

EXAMPLE 37

A mixture of 2.0 g. of 2-acetyl-7-[2-hydroxy-3-(N-acetyl-N-isopropyl)aminopropoxy]benzofuran and 10 ml. of 2 N hydrochloric acid was heated at 70° to 80° C. for 2 hours. After cooling, the reaction mixture was washed with ether, made alkaline with 1.3 N aqueous sodium hydroxide solution and extracted with etherchloroform. The organic layer was washed with water, dried over anhydrous sodium sulfate and the solvent was evaporated under a reduced pressure to give 1.92 g. of 2-acetyl-7-(2-hydroxy-3-isopropylaminopropoxy)benzofuran having a melting point of 113° to 115° C.

EXAMPLE 38

In 10 ml. of 10aqueous dioxane was dissolved 1.0 g. of 2-(1-ethylenedioxy)ethyl-7-(2-oxo-3-isopropylaminopropoxy)benzofuran and thereto was added in portions 100 mg. of sodium borohydride with agitation under cooling. The mixture was reacted at a room temperature for 30 minutes and thereto was added 4 drops of acetic acid. After filtration, 4 drops of concentrated hydrochloric acid was added to the filtrae and the mixture was agitated at a room temperature for 15 minutes and then the solvent was evaporated under a reduced pressure. To the residue was added 1.3 N aqueous sodium hydroxide solution to make alkaline and then the mixture was extracted with etherchloroform. The organic layer was washed with water, dried over anhydrous sodium sulfate and the solvent was evaporated under a reduced pressure. The residue was allowed to stand at a room temperature to give 0.9 g. of 2-acetyl-7-(2-hydroxy-3-isopropylaminopropoxy)benzofuran having a melting point of 113° to 115° C.

EXAMPLE 39

In 30 ml. of ethanol was dissolved 1.0 g. of 2-(1-ethylenedioxy)ethyl-7-[2-hydroxy-3-(N-benzyl-N-isopropyl)aminopropoxy] benzofuran and thereto was added 0.5 g. of 5 % palladium-charcoal. To the mixture was added hydrogen gas at a room temperature under atmospheric pressure until theoretical amount of hydrogen gas was absorbed. After filtration, the filtrate was distilled under a reduced pressure to give 0.65 g. of clear oily substance. The substance thus obtained was dissolved in 5 ml. of ethanol and thereto was added 2 drops of concentrated hydrochloric acid. The mixture was agitated at a room temperature for 30 minutes and then the solvent was evaporated under a reduced pressure. To the residue was added 5 ml. of 3 N hydrochloric acid. The mixture was extracted three times with each 15 ml. of ether, made alkaline with 1.3 N aqueous sodium hydroxide solution, extracted twice with each 25 ml. of ether. The solvent was evaporated to give 0.51 g. of 2-acetyl-7-(2-hydroxy-3-isopropylaminopropoxy)benzofuran having a melting point of 113° to 115° C.

EXAMPLE 40

To 20 ml. of ethanol was suspended 0.25 g. of platinum oxide and thereto was added hydrogen gas at a room temperature. To the mixture was added a solution of 0.6 g. of 2-(1-ethylenedioxy)ethyl-7-(2-oxo-3-hydroxyiminopropoxy)benzofuran in 10 ml. of ethanol and 5 ml. of acetone. To the mixture was added with agitation hydrogen gas at a room temperature under atmospheric pressure until theoretical amount of hydrogen was absorbed. After filtration, to the filtrate was added 4 drops of concentrated hydrochloric acid. The mixture was agitated at a room temperature for 15 minutes and then the solvent was evaporated under a reduced pressure. To the residue was added 10 ml. of 0.5 N hydrochloric acid and the mixture was extracted with ether. The aqueous layer was made alkaline with 2 N aqueous sodium hydroxide solution and extracted with ether. The ether layer was washed with water, dried over anhydrous sodium sulfate and the solvent was evaporated under a reduced pressure to give 0.45 g. of 2-acetyl-7-(2-hydroxy-3-isopropylaminopropoxy)benzofuran having a melting point of 113° to 115° C.

EXAMPLE 41

In 50 ml. of ethanol were dissolved 2.3 g. of 2-(1-ethylenedioxy)ethyl-7-(2,3-dioxopropoxy)benzofuran and 8 g. of isopropylamine. To the mixture was added in portions 1.8 g. of sodium borohydride with agitation at 10° C. over 15 minutes. The mixture was reacted at a room temperature for one hour and thereto was added 4 drops of acetic acid. To the mixture was added 150 ml. of 2 N hydrochloric acid and the mixture was extracted with ether. The aqueous layer was neutralized with 1.0 N aqueous sodium hydroxide solution and extracted with ether. The ether layer was washed with water, dried over anhydrous sodium sulfate and the solvent was evaporated under a reduced pressure to give 0.9 g. of 2-acetyl-7-(2-hydroxy-3-isopropylaminopropoxy)-benzofuran having a melting point of 113° to 115° C.

EXAMPLE 42

To 30 g. of acetic acid were added 1 g. of 2-(1-ethylenedioxy)ethyl-7-(2-cyano-2-hydroxyethoxy)benzofuran, 20 g. of acetone and 1.2 g. of 5 % palladium-charcoal and thereto was added with agitation hydrogen gas at a room temperature under atmospheric pressure for 24 hours. The mixture was filtered and the solvent was evaporated under a reduced pressure. To the residue was added 40 ml. of 1.3 N aqueous sodium hydroxide solution and the mixture was refluxed for 15 minutes. After cooling, the mixture was extracted with ether-chloroform and the organic layer was washed with water, dried over anhydrous sodium hydroxide solution and the solvent was evaporated under a reduced pressure to give 0.3 g. of 2-acetyl-7-(2-hydroxy-3-isopropylaminopropoxy)benzofuran having a melting point of 113° to 115° C.

EXAMPLE 43

A mixture of 6.25 parts by weight of 2-acetyl-7-(2-hydroxy-3-isopropylaminopropoxy)benzofuran, 84.4 parts by weight of lactose, 8.75 parts by weight of Avicel (The registered trade mark of a microcrystalline cellulose made by Asahi Chemical Industry Co., Ltd.), 0.5 parts by weight of magnesium stearate and 0.1 part by weight of Aerosil (The commercial name of a finely devided silicon dioxide made by Nippon Aerosil Kabushiki Kaisha) was thoroughly blended. The resulting powder was filled into capsules made of gelatin to give capsules containing 5 mg. of the essential active ingredient per one capsule.

EXAMPLE 44

The same procedure as in Example 43 was repeated except that a mixture of 12.5 parts by weight of 2-acetyl-7-(2-hydroxy-3-isopropylaminopropoxy)benzofuran, 77.3 parts by weight of lactose, 9.4 parts by weight of Avicel, 0.63 part by weight of magnesium stearate and 0.19 part by weight of silicon dioxide was employed to give capsules containing 10 mg. of the essential active ingredient per one capsule.

EXAMPLE 45

The same procedure as in Example 43 was repeated except that a mixture of 12.5 parts by weight of 2-acetyl-7-(2-hydroxy-3-isopropylaminopropoxy)benzofuran, 74.4 parts by weight of lactose, 8.75 parts by weight of Avicel, 2.88 parts by weight of talc and 1.5 parts by weight of magnesium stearate was employed to give capsules containing 10 mg. of the essential active ingredient per one capsule.

EXAMPLE 46

The same procedure as in Example 43 was repeated except that a mixture of 20 parts by weight of 2-acetyl-7-(2-hydroxy-3-isopropylaminopropoxy)benzofuran, 71.4 parts by weight of lactose, 8 parts by weight of Avicel and 0.6 part by weight of magnesium stearate was employed to give capsules containing 20 mg. of the essential active ingredient per one capsule.

EXAMPLE 47

The same procedure as in Example 43 was repeated except that 6.25 parts by weight of 2-acetyl-7-(2-hydroxy-3-isopropylaminopropoxy)benzofuran hydrochloride was employed instead of its free base to give capsules containing 5 mg. of the essential active ingredient per one capsule.

EXAMPLE 48

A mixture of 20.0 parts by weight of 2-acetyl-7-(2-hydroxy-3-isopropylaminopropoxy)benzofuran, 63.0 parts by weight of lactose, 15.0 parts by weight of Avicel and 1.0 part by weight of magnesium stearate was thoroughly blended and then screened through a 50 mesh screen. The resulting powder was tabletted by an automatic tabletting machine to give tablets containing 20 mg. of the essential active ingredient per one tablet.

EXAMPLE 49

The same procedure as in Example 48 was repeated except that 2-acetyl-7-(2-hydroxy-3-tert.-butylaminopropoxy)benzofuran, 2-acetyl-7-(2-hydroxy-3-sec.-butylaminopropoxy)benzofuran, 2-carbethoxy-7-(2-hydroxy-3-isopropylaminopropoxy)benzofuran, 2-benzoyl-7-(2-hydroxy-3-isopropylaminopropoxy)benzofuran, 2-acetyl-3-(2-hydroxy-3-tert.-butylaminopropoxy)benzofuran, 2-acetyl-4-(2-hydroxy-3-tert.-butylaminopropoxy)benzofuran, 2-acetyl-5-(2-hydroxy-3-isopropylaminopropoxy)benzofuran, 2-acetyl-6-(2-hydroxy-3-tert.-butylaminopropoxy)benzofuran, 2-(1-isopropyliminoethyl)-7-(2-hydroxy-3-isopropylaminopropoxy)benzofuran, 2-(1-isopropyliminoethyl)-4-(2-hydroxy-3-isopropylaminopropoxy)benzofuran, 2-(1-sec.-butyliminoethyl)-7-(2-hydroxy-3-sec.-butylaminopropoxy)benzofuran, 2-(1-sec.-butyliminoethyl)-4-(2-hydroxy-3-sec.-butylaminopropoxy)benzofuran and 2-ethyl-4-acetyl-7-(2-hydroxy-3-isopropylaminopropoxy)benzofuran were employed respectively instead of 2-acetyl-7-(2-hydroxy-3-isopropylaminopropoxy)benzofuran to give 13 kinds of tablets containing 20 mg. of each essential active ingredient per one tablet.

EXAMPLE 50

The tablets obtained in Example 48 were crushed and then screened through a 50 mesh screen and a 100 mesh screen to give granules having particle sizes of 50 meshes to 100 meshes which contain 200 mg. of the essential active ingredient per 1 g. of granules.

EXAMPLE 51

The mixture employed in Example 43 was finely pulverized and then screened through a 100 mesh screen to give powders having a mean particle size of 120 meshes which contain 62.5 mg. of the essential active ingredient per 1 g. of powders.

EXAMPLE 52

Into 2000 parts by volume of a physiological salt solution was dissolved 1 part by weight of 2-acetyl-7-(2-hydroxy-3-isopropylaminopropoxy)benzofuran to give an injection.

EXAMPLE 53

Into 1000 part by volume of a physiological salt solution was dissolved 1 part by weight of 2-acetyl-7-(2-hydroxy-3-isopropylaminopropoxy)benzofuran hydrochloride to give an injection.

EXAMPLE 54

With respect to the present benzofuran derivatives and propranolol which has been widely employed as an $\beta$-adrenergic blocking agent, there was tested isoproterenol antagonism concerning myocardial contractile force, heart rate and diastolic blood pressure in anesthetized dogs (Cf. The Journal of Pharmacology and Experimental Therapeutics, Vol. 176, No. 2, pages 339 to 349, 1971).

The benzofuran derivatives employed are as follows:
Compound No. 1: 2-(1-isopropyliminoethyl)-7-(2-hydroxy-3-isopropylaminopropoxy)benzofuran
Compound No. 2: 2-acetyl-4-(2-hydroxy-3-tert.-butylaminopropoxy)benzofuran
Compound No. 3: 2-acetyl-7-(2-hydroxy-3-isopropylaminopropoxy)benzofuran
Compound No. 4: 2-acetyl-7-(2-hydroxy-3-tert.-butylaminopropoxy)benzofuran
Compound. No. 5: 2-carbethoxy-7-(2-hydroxy-3-isopropylaminopropoxy)benzofuran
Compound No. 6: 2-(1-isopropyliminoethyl)-4-(2-hydroxy-3-isopropylaminopropoxy)benzofuran
Compound No. 7: 2-acetyl-7-(2-hydroxy-3-sec.-butylaminopropoxy)benzofuran
Compound No. 8: 2-ethyl-4-acetyl-7-(2-hydroxy-3-isopropylaminopropoxy)benzofuran
Compound No. 9: 2-(1-sec.-butyliminoethyl)-7-(2-hydroxy-3-sec.-butylaminopropoxy)benzofuran
Compound No. 10: 2-(1-sec.-butyliminoethyl)-4-(2-hydroxy-3-sec.-butylaminopropoxy)benzofuran This numbering of the compounds is also held with the following Examples 55 to 56.

Male and female dogs weighing 9 kg. to 20 kg. were employed. The dogs were anesthetized with barbital sodium (30 mg./kg.) given intraperitoneally. The compounds to be tested and isoproterenol were administered in femoral vein through a canula.

Isoproterenol was administered in a dose of 0.3 $\mu$g./kg., by which an increase in myocardial contractile force, an increase in heart rate and a decrease in diastolic blood pressure were caused. The maximum increase was adopted as the increase in myocardial contractile force. The increase after 1 minute from the administration of isoproterenol was adopted as the increase in heart rate. The maximum decrease was adopted as the decrease in diastolic blood pressure.

Then, the compounds to be tested were administered in a dose of 0.01 to 100 $\mu$g./kg. After an interval of 2 minutes, isoproterenol was again administered in a dose of 0.3 $\mu$g./kg. After the second administration of isoproterenol, the maximum increase in myocardial contractile force, the increase after 1 minute from the administration of isoproterenol in heart rate and the maximum decrease in diastolic blood pressure were again determined. 50% inhibitions [$ED_{50}$ ($\mu$g./kg.)] by each compound in the increase in myocardial contractile force, in the increase in heart rate and in the decrease in diastolic blood pressure, were calculated from the values after the first administration of isoproterenol and the values after the second administration of isoproterenol. Further, the relative activities in isoproterenol antagonism of the compounds when the activity of Propranolol is 1 were calculated from the 50% inhibitions.

The results are shown in Table I.

Table I

| Compound No. | Inhibition of increase in myocardial contractile force | | Inhibition of increase in heart rate | | Inhibition of decrease in diastolic blood pressure | |
|---|---|---|---|---|---|---|
| | $ED_{50}$($\mu$g./kg.) | Relative activity | $ED_{50}$($\mu$g./kg.) | Relative activity | $ED_{50}$($\mu$g./kg.) | Relative activity |
| 1 | 0.60 | 15.9 | 0.42 | 25.0 | 0.30 | 3.1 |
| 2 | 8.62 | 1.1 | 35.2 | 0.3 | 0.92 | 1.0 |
| 3 | 3.40 | 2.8 | 0.52 | 21.0 | 0.18 | 5.3 |
| 4 | 6.33 | 1.5 | 3.50 | 3.0 | 0.72 | 1.3 |
| 5 | 9.50 | 1.0 | 0.21 | 50.0 | 1.57 | 0.6 |
| 6 | 5.93 | 1.6 | 0.21 | 50.0 | 0.03 | 30.2 |
| 7 | 5.59 | 1.7 | 7.07 | 1.5 | 2.35 | 0.4 |
| 8 | 6.40 | 1.5 | 0.30 | 35.0 | 1.90 | 0.5 |
| 9 | 0.73 | 13.1 | 0.53 | 20.0 | 0.16 | 6.0 |
| 10 | 3.95 | 2.4 | 0.21 | 50.0 | 0.04 | 23.5 |
| Propranolol | 9.50 | 1.0 | 10.6 | 1.0 | 0.94 | 1.0 |

EXAMPLE 55

With respect to the present benzofuran derivatives and Propranolol, there was tested isoproterenol antagonism concerning myocardial contractile force and heart rate in isolated guinea-pig atria (Cf. The Journal of Pharmacology and Experimental Therapeutics, Vol. 168, No. 1, pages 116 to 126, 1969).

Isolated guinea-pig atrium was mounted in a chamber containing Ringer-Locke solution (37° C.), through which a mixed gas of 95% $O_2$ and 5% $CO_2$ was continuously bubbled. Isoproterenol was added to the solution at a concentration of $1 \times 10^{-8}$ g./ml. 50% inhibitions of isopreterenol responses and relative activities were determined by the same manner as described in Example 54. The results are shown in Table II.

Table II

| Compound No. | Inhibition of increase in heart rate | | Inhibition of increase in myocardial contractile force | |
|---|---|---|---|---|
| | $ED_{50}$ (g./ml.) | Relative activity | $ED_{50}$ (g./ml.) | Relative activity |
| 1 | $1.4 \times 10^{-8}$ | 7.1 | $1.7 \times 10^{-9}$ | 5.9 |
| 2 | $4.5 \times 10^{-8}$ | 2.2 | $1.7 \times 10^{-8}$ | 0.6 |
| 3 | $4.0 \times 10^{-8}$ | 2.5 | $5.0 \times 10^{-9}$ | 2.0 |
| 4 | $3.3 \times 10^{-8}$ | 3.0 | $4.0 \times 10^{-9}$ | 2.5 |
| 5 | $2.9 \times 10^{-8}$ | 3.5 | $5.5 \times 10^{-9}$ | 1.8 |
| 6 | $1.4 \times 10^{-8}$ | 7.0 | $8.0 \times 10^{-9}$ | 1.3 |
| 7 | $6.7 \times 10^{-8}$ | 1.5 | $4.8 \times 10^{-9}$ | 2.0 |
| 8 | $5.3 \times 10^{-8}$ | 1.9 | $9.1 \times 10^{-9}$ | 1.1 |
| 9 | $6.0 \times 10^{-8}$ | 1.6 | $4.0 \times 10^{-9}$ | 2.5 |
| 10 | $4.0 \times 10^{-8}$ | 2.5 | $5.9 \times 10^{-9}$ | 1.7 |
| Propranolol | $1.0 \times 10^{-7}$ | 1.0 | $1.0 \times 10^{-8}$ | 1.0 |

EXAMPLE 56

Acute toxicities of the present benzofuran derivatives and Propranolol were tested in mice. The compounds to be tested were administered by injecting intravenously a 0.9% physiological salt solution of the compound. $LD_{50}$ after 24 hours from the administration of the compound was determined. The results are shown in Table III.

Table III

| Compound No. | $LD_{50}$ (mg./kg.) |
|---|---|
| 1 | 65 – 70 |
| 2 | 35 – 40 |
| 3 | 100 – 105 |
| 4 | 45 – 55 |
| 5 | 50 – 55 |
| 6 | 45 – 50 |
| 7 | 75 – 80 |
| 8 | 120 – 125 |
| 9 | 75 – 80 |
| 10 | 60 – 65 |
| Propranolol | 25 – 30 |

EXAMPLE 57

Clinical study of cardiac arrhythmias

A clinical study relating to cardiac arrhythmias was made covering the patients shown in Table IV. The active ingredient, 2-acetyl-7-(2-hydroxy-3-isopropylaminopropoxy)benzofuran hydrochloride, contained in the capsules obtained in Example 47 was administrered orally in a dose of 30 to 60 mg./day for a period of 10 days to 12 weeks. The results thereof are shown in Table IV. The treatment evaluation was determined according to the following standard:

Extremely effective (++): An outstanding improvement of subjective symptom and an outstanding improvement in electrocardiogram were observed.

Effective (+): Therapeutic effects were clearly observed.

Slightly effective (±): Subjective symptom was fairly decreased and some improvement in electrocardiogram was observed.

Non-effective (−): Any therapeutic effect was not observed.

Table IV

| Patient No. | Age | Sex | Basic disease | Kind of cardiac arrhythmias | Dose (mg./day) | Period for treatment |
|---|---|---|---|---|---|---|
| 1 | 45 | F | Hypertension | Ventricular extrasystole | 60 | 3 W |
| 2 | 47 | M | Hypotension | Ventricular extrasystole | 60 | 2 W |
| 3 | 46 | M | Hypotension | Ventricular extrasystole | 60 | 5 W |
| 4 | 70 | M | Hypertension | Auricular extrasystole | 60 | 2 W |
| 5 | 61 | F | Hypertension | Ventricular extrasystole | 60 | 10 day |
| 6 | 65 | M | Hypertension | Ventricular extrasystole | 60 | 4 W |
| 7 | 61 | F | Hypertension | Ventricular extrasystole | 60 | 5 W |
| 8 | 61 | F | Mitral stenosis | Ventricular extrasystole | 45 | 2 W |
| 9 | 44 | M | Mitral stenosis | Auricular fibrillation | 60 | 3 W |
| 10 | 65 | F | Coronary insufficiency | Auricular extrasystole | 30 | 12 W |
| 11 | 66 | M | Myocardial infarction | Ventricular extrasystole | 60 | 2 W |

| Patient No. | Heart rate/min. Before treatment | Heart rate/min. After treatment | Blood pressure (mmHg) Before treatment | Blood pressure (mmHg) After treatment | Side effect | Treatment evaluation |
|---|---|---|---|---|---|---|
| 1 | 72 | 60 | 112/64 | 96/66 | No | + |
| 2 | 66 | 60 | 116/70 | 114/70 | No | ± |
| 3 | 88 | 82 | 98/64 | 104/62 | No | − |
| 4 | 75 | 68 | 176/104 | 130/70 | No | ++ |
| 5 | 82 | 72 | 165/86 | 145/78 | No | ± |
| 6 | 120 | 60 | 206/130 | 154/110 | No | + |
| 7 | 86 | 76 | 200/82 | 165/78 | No | + |
| 8 | 98 | 64 | 140/85 | 125/75 | No | + |
| 9 | 120 | 100 | 124/80 | 108/66 | No | ± |
| 10 | 80 | 60 | 152/86 | 135/80 | No | ± |
| 11 | 84 | 68 | 132/90 | 118/68 | No | ± |

EXAMPLE 58

Clinical study of angina pectoris

A clinical study relating to angina pectoris was made covering the patients shown in Table V. The active ingredient, 2-acetyl-7-(2-hydroxy-3-isopropylaminopropoxy)benzofuran hydrochloride, contained in the capsules obtained in Example 47 was administered orally in a dose of 15 to 60 mg./day for a period of 1 to 10 weeks. The results thereof are shown in Table V.

Table V

| Patient No. | Age | Sex | Complication | Dose (mg./day) | Period for treatment | Treatment evaluation |
|---|---|---|---|---|---|---|
| 1 | 68 | M | Hypertension | 15 | 2 W | ± |
| 2 | 54 | M | Pyelitis | 15 | 11 W | + |
| 3 | 71 | F | Hypertension | 30 | 10 W | + |
| 4 | 46 | F | Hypertension | 30 | 10 W | + |
| 5 | 51 | F | Hypertension | 30 | 8 W | + |
| 6 | 31 | F | Chronic pancreatitis | 15 | 1 W | − |
| 7 | 54 | M | Hypertension | 60 | 6 W | + |
| 8 | 70 | M | Hypertension | 60 | 10 W | + |
| 9 | 65 | M | — | 30 | 4 W | ++ |
| 10 | 35 | M | — | 30 | 4 W | ++ |
| 11 | 51 | M | — | 60 | 3 W | + |
| 12 | 75 | F | Auricular extrasystole | 30 | 4 W | ++ |
| 13 | 58 | M | Mitral stenosis | 30 | 2 W | + |
| 14 | 61 | M | Aortic insufficiency | 60 | 4 W | ++ |
| 15 | 60 | M | — | 30 | 2 W | ++ |

EXAMPLE 59

Clinical study of hypertension

To a male patient of 68 age who was diagnosed as an essential hypertension was orally administered the active ingredient, 2-acetyl-7-(2-hydroxy-3-isopropyl aminopropoxy)benzofuran hydrochloride, contained in the capsules obtained in Example 47 in a dose of 60 mg./day for 35 days. As a result, the maximum blood pressure of 210 mmHg and the minimum blood pressure of 88 mmHg before treatment were decreased to 176 mmHg and 76 mmHg after treatment, respectively.

To four hypertensive patients was orally administered the active ingredient, 2-acetyl-7-(2-hydroxy-3-isopropylaminopropoxy)benzofuran hydrochloride, contained in the capsules obtained in Example 47 in a dose of 60 mg./day for 30 days. with three patients among four, good therapeutic results were obtained.

The treatment evaluation was determined according to the following standard:

Extremely effective (++): The pulse rate before treatment was decreased in a difference of not less than 20 after treatment.

Effective (+): The pulse rate before treatment was decreased in a difference of 10 to 19 after treatment.

Non-effective (−): The pulse rate before treatment was decreased in a difference of less than 10 after treatment.

For reference, a therapeutic effect of an antihyperthyroidism medicament to tachycardia in hyperthyroidism in case of its single administration was investigated.

To 12 patients of hyperthyroidism shown in Table VII was orally administered Mercazol which has been widely employed as an antihyperthyroidism medicament in a dose of 30 mg./day for 14 days. The results thereof are shown in Table VII.

Table VI

| Patient No. | Age | Sex | Function test of thyroid gland before treatment | | | Pulse rate | | | Treatment evaluation | Side effect |
|---|---|---|---|---|---|---|---|---|---|---|
| | | | BEI ($\mu$g./dl.) | Triosorb (%) | Tetrasorb ($\mu$g./dl.) | Before treatment | After treatment | Difference | | |
| 1 | 18 | F | 12.4 | 54.0 | Above 25.0 | 102 | 80 | 22 | ++ | No |
| 2 | 23 | F | 11.6 | 56.1 | 10.4 | 140 | 108 | 32 | ++ | No |
| 3 | 14 | F | 11.2 | 39.1 | 19.4 | 102 | 88 | 14 | + | No |
| 4 | 49 | F | 10.8 | 43.2 | 17.0 | 130 | 100 | 30 | ++ | No |
| 5 | 34 | F | 10.5 | 33.8 | 17.0 | 128 | 77 | 51 | ++ | No |
| 6 | 42 | F | 12.6 | 42.7 | 19.5 | 108 | 80 | 28 | ++ | No |
| 7 | 32 | F | 8.7 | 34.3 | 11.6 | 100 | 76 | 24 | ++ | No |
| 8 | 18 | F | 13.9 | 52.9 | Above 25.0 | 120 | 100 | 20 | ++ | No |
| 9 | 48 | F | 11.8 | 48.1 | — | 120 | 100 | 20 | ++ | No |
| 10 | 37 | M | 10.1 | 45.5 | 11.2 | 128 | 108 | 20 | ++ | No |
| 11 | 33 | F | 7.4 | 38.8 | 14.7 | 92 | 84 | 8 | — | No |
| 12 | 45 | F | 7.2 | 47.2 | — | 104 | 88 | 16 | + | No |
| Average | | | | | | 114.5 | 90.4 | 23.8 | | |
| Standard deviation | | | | | | 14.4 | 11.6 | 1.1 | | |

Table VII

| Patient No. | Age | Sex | Function test of thyroid gland before treatment | | Pulse rate | | |
|---|---|---|---|---|---|---|---|
| | | | BEI ($\mu$g./dl.) | Triosorb (%) | Before treatment | After treatment | Difference |
| 1 | 15 | F | 12.2 | — | 110 | 90 | 20 |
| 2 | 55 | F | 17.2 | — | 132 | 110 | 22 |
| 3 | 29 | F | 17.9 | — | 110 | 100 | 10 |
| 4 | 50 | F | BMR + 77 % | — | 104 | 90 | 14 |
| 5 | 22 | F | 12.0 | — | 110 | 100 | 10 |
| 6 | 39 | F | 13.4 | — | 120 | 108 | 12 |
| 7 | 25 | F | 11.3 | — | 110 | 100 | 10 |
| 8 | 19 | M | 13.9 | — | 100 | 90 | 10 |
| 9 | 51 | F | 14.8 | 48.7 | 100 | 90 | 10 |
| 10 | 16 | F | 14.2 | 43.1 | 120 | 108 | 12 |
| 11 | 21 | F | 9.4 | — | 120 | 116 | 4 |
| 12 | 22 | F | 14.1 | — | 100 | 100 | 0 |
| Average | | | | | 111.3 | 100.2 | 12.0 |
| Standard deviation | | | | | 9.6 | 8.6 | 0.6 |

EXAMPLE 60

Clinical study of hyperthyroidism

A. A therapeutic effect of the present pharmaceutical composition to tachycardia in hyperthyroidism in case of its signle administration was investigated.

To 12 patients of hyperthyroidism shown in Table VI was orally administered the active ingredient, 2-acetyl-7-(2-hydroxy-3-isopropylaminopropoxy)benzofuran hydrochloride, contained in the capsules obtained in Example 47 in a dose of 30 mg./day (3 times per day) for 14 days. The results thereof are shown in Table VI.

(B) A therapeutic effect of the present pharmaceutical composition in combination with an antihyperthyroidism medicament to tachycardia in hyperthyroidism was investigated.

To six patients of hyperthyroidism shown in Table VIII were orally administered the active ingredient, 2-acetyl-7-(2-hydroxy-3-isopropylaminopropoxy)benzofuran hydrochloride, contained in the capsules obtained in Example 47 and Mercazol in each dose of 30 mg./day (three times per day) for 14 days. The results thereof are shown in Table VIII.

Table VIII

| Patient No. | Age | Sex | Function test of thyroid gland before treatment | | | Pulse rate | | Treatment evaluation | Side effect |
|---|---|---|---|---|---|---|---|---|---|
| | | | BEI (μg./dl.) | Triosorb (%) | Tetrasorb (μg./dl.) | Before treatment | After treatment | | |
| 1 | 33 | F | 7.4  | 38.8 | 14.7 | 100 | 88 | +   | No |
| 2 | 28 | F | 12.7 | 58.3 | 20.2 | 100 | 88 | +   | No |
| 3 | 25 | F | 17.0 | 51.0 | 18.5 | 100 | 76 | + + | No |
| 4 | 34 | M | 17.0 | 54.7 | 16.5 | 100 | 78 | + + | No |
| 5 | 17 | F | 10.0 | 39.5 | 21.0 | 112 | 68 | + + | No |
| 6 | 17 | F | 14.0 | 47.0 | —    | 120 | 82 | + + | No |

What we claim is:

1. A pharmaceutical composition possessing a β-adrenergic blocking activity and local anesthetic activiy which comprises as the essential active ingredient an effective amount a benzofuran derivative of the formula:

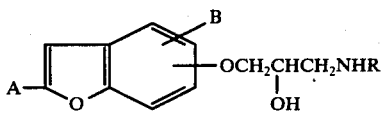

wherein A is —COR',

or ethyl group; B is hydrogen atom when A is —COR' or

or —COR" substituted at the 3 or 4 position of the benzofuran nucleus when A is ethyl; R is an alkyl group having 1 to 5 carbon atoms; R' is an alkyl group having 1 to 4 carbon atoms, an alkoxy group having 1 to 3 carbon atoms or phenyl group; R" is an alkyl group having 1 to 4 carbon atoms, phenyl or phenylalkyl group wherein the alkyl moiety has 1 to 2 carbon atoms; and the substituted propoxy group is at the 3, 4, 5, 6 or 7 position of the benzofuran nucleus; or a pharmacetuically acceptable acid addition salt thereof in admixture with a pharmaceutically acceptable carrier.

2. The pharmaceutical composition of claim 1, which is employed for treating a disease selected from the group consisting of cardiac arrhythmias, angina pectoris, hypertension and hyperthyroidism.

3. The pharmaceutical composition of claim 1, which is administered in a dose of 10 to 200 mg./day on the basis of the essential active ingredient for treating cardiac arrhythmias.

4. The pharmaceutiical composition of claim 1, which is administered in a dose of 10 to 200 mg./day on the basis of the essential active ingredient for treating angina pectoris.

5. The pharmaceutical composition of claim 1, which is administered in a dose of 30 to 800 mg./day on the basis of the essential active ingredient for treating hypertension.

6. The pharmaceutical composition of claim 1, which is administered in a dose of 10 to 100 mg./day on the basis of the essential active ingredient for treating hyperthyroidism.

7. The pharmaceutical composition of claim 1, which is in a preparation form selected from the group consisting of tablet, capsule, powder, granule.

8. The pharmaceutical composition of claim 1, which is in a preparation form selected from the group consisting of solution, suspension, emulsion and syrup.

9. The pharmaceutical composition of claim 1, wherein the essential active ingredient is a benzofuran derivative of the formula (I) in which R is a branched alkyl group having 3 to 4 carbon atoms.

10. The pharmaceutical composition of claim 9, wherein the essential active ingredient is 2-acetyl-7-(2-hydroxy-3-isopropylaminopropoxy)benzofuran or its hydrochloride.

11. The pharmaceutical composition of claim 9, wherein the essential active ingredient is 2-acetyl-7-(2-hydroxy-3-tert.-butylaminopropoxy)benzofuran or its hydrochloride.

12. The pharmaceutical composition of claim 9, wherein the essential active ingredient is 2-acetyl-7-(2-hydroxy-3-sec.-butylaminopropoxy)benzofuran or its hydrochloride.

13. The pharmaceutical composition of claim 9, wherein the essential active ingredient is 2-carbethoxy-7-(2-hydroxy-3-isopropylaminoproxy)benzofuran or its hydrochloride.

14. The pharmaceutical composition of claim 9, wherein the essential active ingredient is 2-benzoyl-7-(2-hydroxy-3-isopropylaminopropoxy)benzofuran or its hydrochloride.

15. The pharmaceutical composition of claim 9, wherein the essential active ingredient is 2-acetyl-3-(2-hydroxy-3-tert.-butylaminopropoxy)benzofuran or its hydrochloride.

16. The pharmaceutical composition of claim 9, wherein the essential active ingredient is 2-acetyl-4-(2-hydroxy-3-tert.-butylaminopropoxy)benzofuran or its hydrochloride.

17. The pharmaceutical composition of claim 9, wherein the essential active ingredient is 2-acetyl-5-(2-hydroxy-3-isopropylaminopropoxy)benzofuran or its hydrochloride.

18. The pharmaceutical composition of claim 9, wherein the essential active ingredient is 2-acetyl-6-(2-hydroxy-3-tert.-butylaminopropoxy)benzofuran or its hydrochloride.

19. The pharmaceutical composition of claim 9, wherein the essential active ingredient is 2-(1-isopropyliminoethyl)-7-(2-hydroxy-3-isopropylaminopropoxy)-benzofuran or its hydrochloride.

20. The pharmaceutical composition of claim 9, wherein the essential active ingredient is 2-(1-isopropyliminoethyl)-4-(2-hydroxy-3-isopropylaminopropoxy)-benzofuran or its hydrochloride.

21. The pharmaceutical composition of claim 9, wherein the essential active ingredient is 2-(1-sec.- butyliminoethyl)-7-(2-hydroxy-3-sec.-butylaminopropoxy)benzofuran or its hydrochloride.

22. The pharmaceutical composition of claim 9, wherein the essential active ingredient is 2-(1-sec.-butyliminoethyl)-4-(2-hydroxy-3-sec.-butylaminopropoxy)benzofuran or its hydrochloride.

23. The pharmaceutical composition of claim 9, wherein the essential active ingredient is 2-ethyl-4-acetyl-7-(2-hydroxy-3-isopropylaminopropoxy)benzofuran or its hydrochloride.

* * * * *